(12) United States Patent
Thauront et al.

(10) Patent No.: US 6,657,077 B1
(45) Date of Patent: Dec. 2, 2003

(54) METHOD FOR PRODUCING A PURIFIED ALKALINE METAL TEREPHTHALATE, DERIVED FROM THE PRODUCTS OF SAPONIFICATION OF POLYTEREPHTHALATES

(75) Inventors: Jacques Thauront, La Garenne-Colombes (FR); Laurent Bonnamich, Lyons (FR); Guy Fraysse, Amberieu en Bugey (FR)

(73) Assignee: Tredi (FR)

( * ) Notice: Subject to any disclaimer, the term of this patent is extended or adjusted under 35 U.S.C. 154(b) by 0 days.

(21) Appl. No.: 09/700,546
(22) PCT Filed: Jan. 28, 1999
(86) PCT No.: PCT/FR99/00175
§ 371 (c)(1), (2), (4) Date: Nov. 16, 2000
(87) PCT Pub. No.: WO99/38835
PCT Pub. Date: Aug. 5, 1999

(30) Foreign Application Priority Data

Jan. 30, 1998 (FR) .............................. 98 01088

(51) Int. Cl.$^7$ .......................... C07C 51/09; C07C 63/14
(52) U.S. Cl. ...................................... 562/483; 562/480
(58) Field of Search ................................. 562/480, 483

(56) References Cited

U.S. PATENT DOCUMENTS

| | | | |
|---|---|---|---|
| 3,544,622 A | | 12/1970 | England |
| 3,952,053 A | * | 4/1976 | Brown, Jr. et al. |
| 4,013,519 A | * | 3/1977 | Hoppert et al. |
| 5,254,666 A | | 10/1993 | Benzaria |

FOREIGN PATENT DOCUMENTS

| | | | |
|---|---|---|---|
| GB | 822834 | * | 11/1959 |
| WO | WO 9529952 | | 11/1995 |
| WO | WO 9724310 | | 7/1997 |
| WO | WO 97/24310 A1 | * | 7/1997 |
| WO | WO 9724312 | | 7/1997 |

* cited by examiner

*Primary Examiner*—Johann Richter
*Assistant Examiner*—Paul A. Zucker
(74) *Attorney, Agent, or Firm*—Hunton & Williams LLP

(57) ABSTRACT

The invention concerns a method for producing terephthalate of alkaline metal and alkylene glycol from recuperated alkylene polyterephthalate. It comprises saponification of said alkylene terephthalates with an aqueous sodium solution, adding a sufficient volume of water to ensure solubilization of the entire alkaline metal terephthalate produced in the reaction medium liquid phase and crystallisation of the sodium terephthalate by concentration of said liquid phase. The resulting sodium terephthalate can be directly used for producing pure terephthalic acid usable for the renewed production of alkylene polyterephthalates to be used in the food industry.

20 Claims, 2 Drawing Sheets

METHOD FOR PRODUCING A PURIFIED ALKALINE METAL TEREPHTHALATE, DERIVED FROM THE PRODUCTS OF SAPONIFICATION OF POLYTEREPHTHALATES

This application is a 35 U.S.C. §371 from PCT/FR99/00175 filed on Jan. 28, 1999, which claims priority from French application FR 9801088 filed Jan. 30, 1998.

The invention relates to an improved process for recovering an alkali metal terephthalate and an alkyene glycol from poly(alkylene terephthalate) waste from used products, for example packaging, films, fibres or bottles, such recovered polyterephthalates possibly also containing other impurities such as fillers, additives, colorants, or being mixed with other solid materials such as paper labels, polyethylene and/or polypropylene closures (for bottles), etc.. The terephthalic acid which can be produced from such polyterephthalate solutions, in particular by precipitation using sulphuric acid, is normally for the production of new poly(alkylene terephthalate)s intended for the production, for example, of new packaging for use in the food industry.

Such processes have already been described in the technical literature. Those which the invention is intended to improve employ alkaline saponification of such poly(alkylene terephthalate)s, usually poly(ethylene terephthalate)s (PET), such saponification leading as a result to the production of an alkali metal polyterephthalate and the corresponding alkylene glycol.

The oldest patents relating to such saponification processes include British patent GB 822 834 in which the saponification reaction is carried out by reacting poly(alkylene terephthalate)s with a relatively dilute solution of an alkali metal hydroxide, in particular sodium hydroxide (an 18% sodium hydroxide solution according to Example 1), the reaction conditions being adjusted so as to encourage maximum salting out of the alkali metal polyterephthalate formed in the reaction solution. Because of the relative solubility of sodium terephthalate, the authors of that patent recommended increasing the salting out capacity of the sodium terephthalate by adding an alcohol, or substituting the aqueous solution with a mixture of an insoluble alkali metal hydroxide and an alcohol.

In French patents 9101025/2672049 and 9213583/2697839, the alkali metal (or alkaline-earth metal) hydroxide is employed in the solid state or in the presence of a quantity of water at least equal in weight to that of the alkali or alkaline-earth metal hydroxide, or in the molten state in the absence of water, the reaction being carried out at a temperature of more than 120° C. and preferably in the range 140° C. to 180° C. The advantage of those processes resides in the possibility of carrying them out continuously.

The alkali metal terephthalate solutions resulting from said saponification operations are usually coloured and mixed with other dissolved matter; hence substantial purification of such solutions has to be carried out before treating them, in particular by acidification, to obtain a terephthalic acid of satisfactory purity.

A further difficulty which until now has not been overcome satisfactorily is recovery of most of the polyol, in particular polyethylene glycol liberated by the saponification reaction. In a solution proposed to that effect in International patent application PCT WO-A-95/29952, the saponification reaction is carried out at a temperature which is higher than the polyol evaporation temperature, in particular over 200° C. The polyol can then be recovered by condensing. In that application, the quality of the alkaline polycarboxylate produced, in particular the sodium terephthalate, is not affected by such high temperatures even if an oxygen-depleted atmosphere is used to control impurity carbonisation reactions at such high temperatures.

The problem of coloration and the amount of other matter dissolved in the alkali metal polycarboxylate solution is not solved by that process. Clearly, the terephthalic acid finally obtained by acid precipitation from the sodium terephthalate solutions obtained cannot be of the desired purity for fresh production of polyethylene glycol polyterephthalate, for example for use for food packaging.

SUMMARY OF THE INVENTION

The aim of the invention is to further improve saponification processes of the type described, in particular to optimise the reaction conditions, to obtain the polycarboxylates more directly, in particular alkali metal polyterephthalates with a purity which is compatible with the demands of the food industry, while employing conditions which demand less energy.

A further aim of the invention is to ensure that the reactions are as complete as possible, such that all of the other principal reactants, in particular the polyols liberated during the saponification operation, are almost completely recovered.

Figure 1:
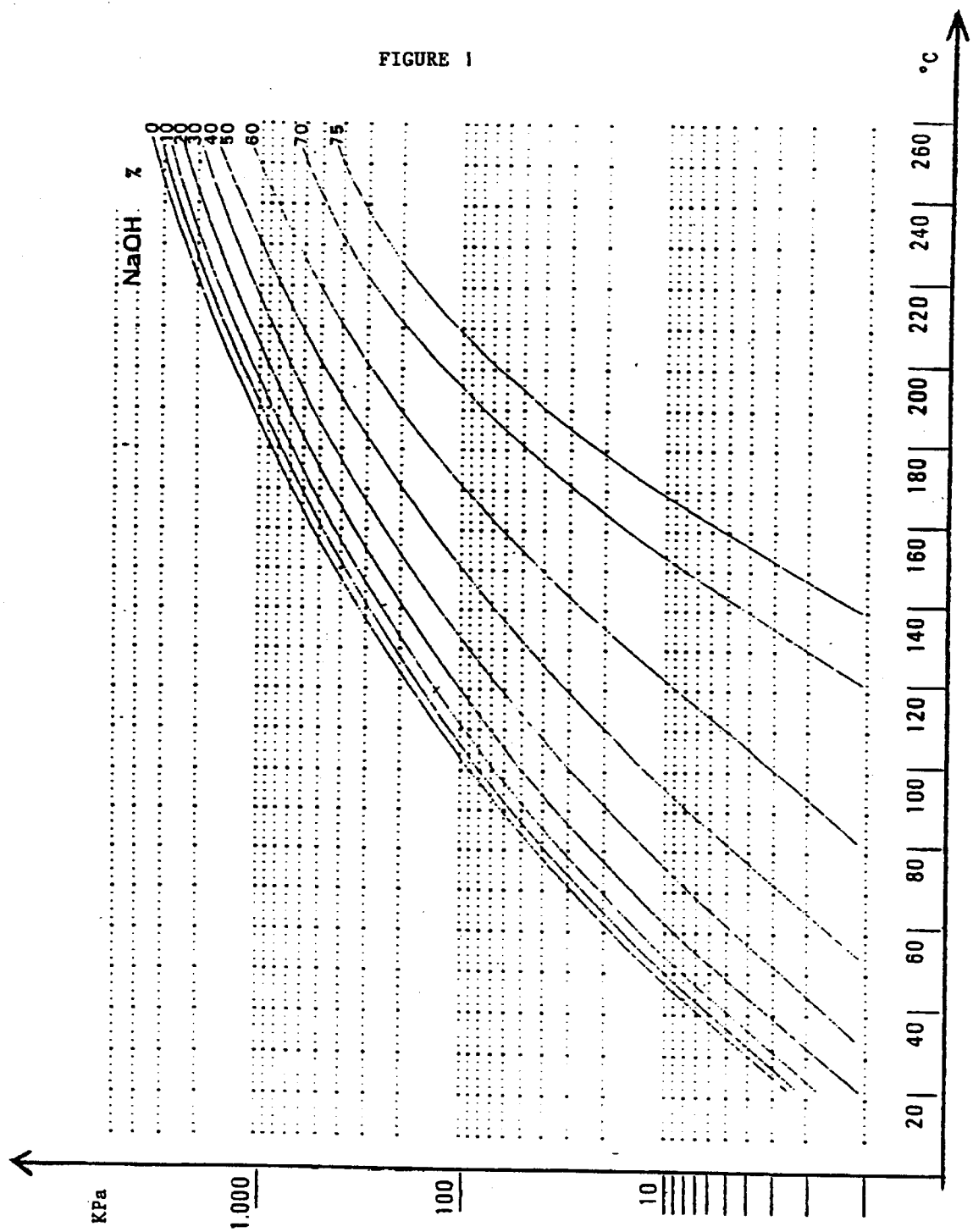
FIG. 1 is a graph showing various curves that illustrate the variations in vapor tensions (in kilopascals) of various sodium hydroxide solutions as a function of temperature.

The process of the invention for producing an aromatic dicarboxylate of an alkali metal, in particular sodium, and an alkylene glycol by alkaline saponification using an alkali metal hydroxide of a polyester of an aromatic dicarboxylic acid, itself derived from a dicarboxylic acid wherein its salt with said alkali metal is soluble in water, is characterized by:

carrying out the saponification step in a liquid medium at a temperature in the range about 120° C. to the boiling point of the corresponding alkylene glycol, if necessary at a pressure which maintains the liquid phase of the reaction medium in the liquid state or at the boiling point at said temperature, preferably throughout the saponification period;

adding a volume of water which is sufficient to ensure dissolution, in particular at the end of the reaction, of all of the alkali metal aromatic dicarboxylate produced in the liquid phase of the reaction medium; and, if necessary after separating the insoluble matter;

concentrating the solution by evaporating off water to cause the major portion of the alkali metal dicarboxylate to crystallise out of the liquid phase then charged with alkylene glycol.

When applied to the production of sodium terephthalate and alkylene glycols from recovered poly(alkylene terephthalate), the process of the invention comprises saponification of these poly(alkylene terephthalate)s with an alkali metal hydroxide, in particular in the form of an aqueous solution, the process then being characterized by:

using an alkali metal hydroxide solution with an initial hydroxide concentration of the order of 20% to of the order of 45% by weight in said saponification reaction;

carrying out the reaction at a temperature in the range about 120° C. to the boiling point of the alkylene glycol produced, if necessary at a pressure which maintains the liquid phase of the reaction medium in the liquid state or at the boiling point of said temperature, for the whole of the saponification period;

adding a volume of water sufficient to ensure dissolution of all of the sodium terephthalate produced in the liquid phase of the reaction medium;

then concentrating the solution by evaporating off water, if necessary after filtering the insoluble matter, to induce crystallisation of the alkali metal terephthalate.

Clearly, the original reaction medium is initially essentially free of the alkylene glycol corresponding to that which is subsequently liberated in the medium after triggering the saponification reaction. Apart from the fact that an initial addition of alkylene glycol would add nothing to the reaction conditions, such an addition would result in much greater salting out of the alkali metal dicarboxylate produced and, as a result, to subsequent addition of a larger volume of water to dissolve the salt before the concentration operation aimed at then inducing crystallisation outside the reaction medium.

Advantageously, the recovered poly(alkylene terephthalate) is gradually introduced in the divided state, in particular in the ground state, into the aqueous solution of the alkali metal hydroxide at its boiling point.

In a preferred implementation of the invention, the alkali metal hydroxide is sodium hydroxide.

In a particularly preferred implementation of the process of the invention, the temperature is in the range 125° C. to 160° C., for example in the range 140° C. to 160° C., and the sodium hydroxide concentration of the solution is in the range 35% to 40% by weight.

The temperature constitutes a particularly important parameter of the reaction. This temperature must be sufficient for the saponification reaction to be properly initiated, then maintained. Choosing the correct range for the initial concentration of the alkali metal solution employed in the reaction means that (1) the reaction medium is effectively maintained in the liquid state or at the boiling point in the temperature range under consideration practically throughout the saponification reaction and especially during the final part of the reaction, at atmospheric pressure or, if necessary, at slightly higher pressures, when the medium is considerably depleted in alkali metal hydroxide, and (2) that the alkylene glycols remain in the reaction medium.

This can be seen by referring to the graph in FIG. 1 which shows curves illustrating the variations in vapour tensions (in kilopascals up the ordinate) of various sodium hydroxide solutions with the proportions by weight indicated in the right hand corner of the figure, as a function of temperature (° C.) along the abscissa.

By operating in the concentration and temperature ranges defined above, it can be seen that the major portion of the reaction can advantageously be carried out at atmospheric pressure or at a pressure which does not exceed 600 kilopascals.

The final concentration step for inducing crystallisation of the alkali metal polycarboxylate can be carried out under reduced pressure and temperature. Because of the quantity of water used to completely re-dissolve the terephthalate produced after the saponification reaction, the impurities, which are also dissolved, but in a very dilute state, remain in solution.

A decisive supplemental advantage of the process of the invention, or more particularly its crystallisation step, is in producing the dicarboxylate directly, in particular the alkali metal terephthalate which after re-dissolving in water leads to a solution the purity of which, if necessary after a single passage over activated charcoal, allows subsequent direct manufacture of the polycarboxylic acid, in particular terephthalic acid, compatible with food applications.

The mother liquors obtained after separating the alkali metal dicarboxylate crystals then already constitute concentrated alkylene glycol solutions.

Preferred modes of carrying out the invention, and a certain number of examples, will be described below with a view to illustrating the possibilities, although these are non-limiting in nature.

Figure 2:
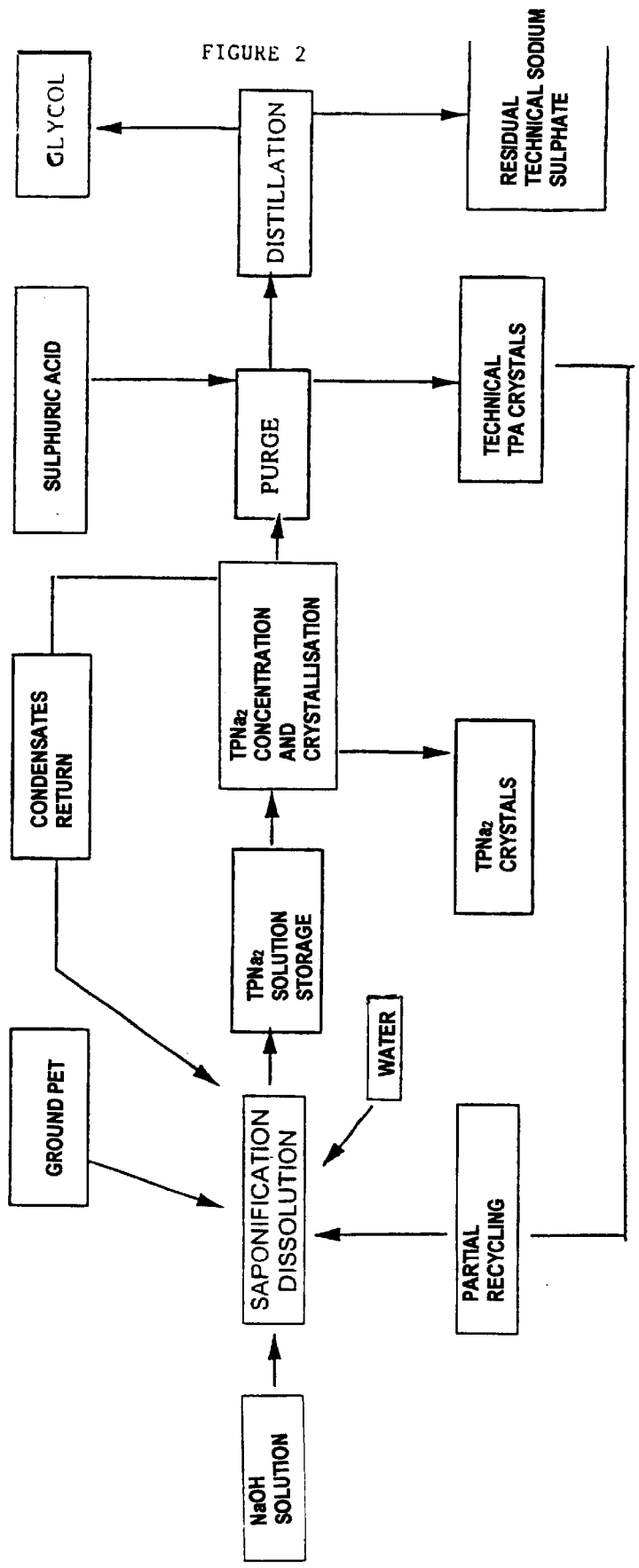
FIG. 2 is a diagram illustrating the major steps in the process of the present invention.

The diagram of FIG. 2 shows the principal steps of such a preferred implementation of the invention in which three steps are carried out. Recovered poly(alkylene terephthalate) is saponified with an alkaline solution at a temperature of 120° C. to 160° C., for example 120° C. to 150° C., or preferably 140° C. to 160° C., this saponification being followed by adding water to obtain a solution of an alkali metal terephthalate and an alkylene glycol. This solution is then concentrated to crystallise the alkali metal terephthalate out of this solution.

Said complete dissolution of the alkaline terephthalate also enables ready separation of the impurities present in used bottles (PVC, polyethylene, polypropylene, pigments, etc.) which have not reacted with the sodium hydroxide.

As already indicated above, it is possible to directly obtain pure alkali metal terephthalate, essentially free of alkylene glycols, by crystallisation from the solution from the saponification step.

Crystallisation of pure alkali metal terephthalates from the solution from the saponification step—if necessary after an intermediate storage step outside the reactor and, if necessary, prior concentration—is advantageously carried out continuously in equipment (crystallisers) which are already available in the industry.

The operation for crystallising the aromatic dicarboxylate, in particular the alkali metal di-terephthalate outside the reaction medium, is preferably carried out at a temperature of 50° C. to 90° C., in particular 60° C., if necessary under partial vacuum.

Preferably, this operation is preceded by a step for concentrating the solution by forced circulation type evaporation, with mechanical re-compression of the fumes by a volumetric compressor at a high temperature (about 100° C.), the already concentrated solution then undergoing said crystallisation under partial vacuum, for example at a temperature of the order of 60° C. (conditions under which the solubility of the dicarboxylate in the crystallisation mother liquor purge is reduced). The water which is then recovered (condensate) can then be recycled to the saponification or dissolution step.

The crystallised alkali metal terephthalate obtained is of sufficient purity, and in particular contains such small quantities of alkylene glycols that it can then be transformed into high purity terephthalic acid (TPA), for example after taking it up into solution in water and acidification, in particular to a pH of 2.5, of the solution obtained using an acid such as sulphuric acid. The terephthalic acid obtained, then itself of high purity, can then be used directly for new polymerisations, jointly with an alkylene glycol, in particular ethylene glycol, to produce food grade plastics materials.

It has been discovered that the presence of alkylene glycols produced in the solution, even in the concentrated state, does not affect the desired purity of the crystallised alkaline terephthalate obtained, which means that the alkylene glycol does not have to be eliminated during the saponification step or prior to dissolving the alkaline terephthalate, while in the majority of prior art processes (for example patents FR-A-2 672 049; FR-A-2 697 839; EP-A-0 597 751; WO-A-95/29952), the alkylene glycol is eliminated or separated prior to this dissolution.

The alkylene glycols can then be recovered from the mother liquors (or purge) after separating the sodium terephthalate crystals. This purge is preferably firstly acidified, in particular treated with sulphuric acid, to a pH of the order of 2.5, to eliminate all traces of sodium hydroxide and to precipitate non food grade terephthalic acid which still contains that purge. The crystals obtained can be used to neutralise the excess sodium hydroxide at the outlet from the saponification reactor. The final filtrate contains alkylene glycol, in particular ethylene glycol, sodium sulphate and acid sodium sulphate. If the acid sodium sulphate is neutralised with liquid sodium hydroxide and then the solution is concentrated by evaporating off the water, sodium sulphate is caused to precipitate out. The liquid is then constituted by a technical grade ethylene glycol (for example for the production of antigels) or is thermally upgraded, since in general it contains no more than 5% of water.

In a variation, after treating the crystallisation mother liquors with sulphuric acid, filtration of the precipitated technical terephthalic acid, the purified alkylene glycol can be recovered from the solution comprising water, sodium sulphate and alkylene glycol, for example by vacuum distillation.

If necessary, at least a portion of the technical grade terephthalate acid obtained is returned to the saponification step or to the step for dissolving the sodium terephthalates produced at the end of the saponification step.

In general, the process of the invention can be carried out as follows:

An alkaline solution, which may or may not have been pre-heated, with a concentration of sodium hydroxide in water in the range about 20% to 45% by weight, is introduced into a stirred reactor. This solution is heated to boiling point at a temperature in the range 115° C. to 140° C., or preferably in the range 140° C. to 60° C. A solution with a sodium hydroxide content of 38% has a boiling point of the order of 130° C.

The ground film and bottle waste is slowly introduced into the reactor until the quantity, expressed as the pure resin, is close to the stoichiometry with respect to the sodium hydroxide, or even slightly lower. In general, this proportion varies from 0.8 times the stoichiometry to 1.5 times the stoichiometry. As an example, the proportion of sodium hydroxide—or more generally the alkali hydroxide—does not exceed 1.2 times the stoichiometry.

As the alkylene terephthalate is introduced, the reactor is kept to temperature by external heating and/or internal heating and, if necessary, the pressure is adjusted to a value which keeps the medium boiling. Steam is condensed in a reflux condenser associated with the reactor so as to keep the initial water content constant.

At the end of the saponification reaction, a sufficient quantity of water is introduced to produce a solution of alkaline terephthalate of the order of 10%.

After separating the impurities present in the initial waste by successive filtration steps, the solution obtained containing the alkaline terephthalate, glycols and excess sodium hydroxide is stored.

The prepared solution is then continuously sent to a crystalliser. The crystals of alkaline terephthalate are separated, washed with water and are in a sufficiently pure state to be used directly for the production of terephthalic acid.

The following examples are given by way of illustration and in no way limit the present invention.

EXAMPLES

I—SAPONIFICATION OF SODIUM TEREPHTHALATE SOLUTION 1.1 Laboratory Tests

Two tests (Examples 1 and 2) were carried out at atmospheric pressure. In both cases, 80 g of PET was mixed with 80 g of 45% sodium hydroxide in a flask provided with a reflux condenser and heated with an oil bath. After reacting for three hours at a temperature of 130° C., the respective yields were:

| test n° 1 | 48% |
|---|---|
| test n° 2 | 70%. |

Only the geometry of the stirrer changed from test n° 1 to test n° 2, the stirring efficiency being better for test n° 2 than for test n° 1.

A pressure test (Example 3) was carried out with the same quantities of reactants. The temperature of the oil bath was kept at 150° C. and the pressure was about 200 kPa.

After 45 minutes of reaction, the observed yield was 85%.

1.2 Semi-industrial Tests.

Two tests were carried out under atmospheric pressure in a stirred reactor with a volume of 1400 litres provided with a reflux condenser.

Example 4

101.6 kilos of 45% sodium hydroxide were introduced into a 1400 litre double envelope reactor and pre-heated with steam circulating in the double envelope of the reactor at 300 kPa. When the temperature of the solution had exceeded 100° C., 110 kilos of PET were added over two and a half hours, the temperature dropping to about 110° C. after having been raised to 124° C. After cooling, water was added (about 750 litres) to obtain 1100 litres of filtrate with the following composition:

NaOH: 1.02%; TPNa$_2$: 7.46%; glycol: 2.1%.

The recovery yield obtained, expressed as the ratio of the weight of the solution multiplied by the concentration of TPNa$_2$ to the weight of PET used multiplied by the ratio 192/210, was 72%.

Example 5

In order to demonstrate the overwhelming effect of the temperature of the reaction medium on the yield, 102 kilos of 50% sodium hydroxide were introduced into the same reactor as that described in Example 4.

After pre-heating to about 100° C., 90 kilos of ground PET were introduced until the temperature started to fall. During this example, the temperature of the reaction mixture was raised to 130° C., as opposed to 124° C in Example 4.

After cooling, water was added to obtain 879 litres of filtrate with the following composition:

NaOH: 1.96%; TPNa$_2$: 9.84%; glycol: 3%.

The yield obtained, calculated as described in Example 4, was 90% as opposed to 72% in Example 4.

Example 6

1.3 Pilot Test

6950 g of 30% by weight sodium hydroxide was heated to 110° C. in a stirred reactor with a volume of 70 litres provided with a reflux condenser and resistance heating. 5000 g of PET was introduced, corresponding to stoichiometry. The reactor was closed then heated; the pressure was maintained at a value of 500 kilopascals for one hour using a reflux condenser. After cooling, 42.7 kg of water was introduced into the reactor. The filtrate obtained after sieving had the following composition:

NaOH: 0.16%; $TPNa_2$: 9.74%; glycol: 2.85%.

The yield obtained, calculated as described in Example 4, was 95%.

II—CRYSTALLISATION OF A SODIUM TEREPHTHALATE SOLUTION

Five two litre batches were vacuum concentrated by a factor of 2 at a temperature of 80° C. from 10 litres of a sodium terephthalate solution with the following principal characteristics from a saponification step:

| | |
|---|---|
| $TPNa_2$ concentration: | 5.02% |
| glycol concentration: | 0.19% |

From the mixture of concentrates, two batches were concentrated by a factor of 2 under the same conditions, and so on until a concentration factor of 16 was obtained.

An analysis of the various products of the last experiment gave the following:

| | Feed | Concentrates | Distillate | Crystals |
|---|---|---|---|---|
| $TPNa_2$ | 12.9% | 4.6% | Traces | 98.19% |
| Glycol | 1.66% | 2.64% | <0.01% | <0.01% |

These results show that the increase in the glycol concentration in the solution from which the crystallisation was carried out did not affect the purity of the $TPNa_2$ finally obtained.

While the foregoing concentrates on the recovery of an alkali metal terephthalate and alkylene glycols from a poly (alkylene terephthalate), the process of the invention can also be applied to other polyesters of aromatic dicarboxylic acids and recovered alkylene, in particular of the type used in the same industries, in particular the food industry, for the production of packaging, films, fibres, bottles, etc. . . . provided that the alkali metal salts, in particular sodium salts, of the corresponding aromatic dicarboxylic acids can be crystallised from the aqueous solutions containing them in the dissolved state under similar conditions to that observed with sodium terephthalate.

Examples of such dicarboxylate polyesters of aromatic alkylenes to which the invention can be applied which can be mentioned are alkylene polyesters containing repeat units from:

isophthalic acid;
  naphthalene dicarboxylic acids, in particular naphthalene 2,6-dicarboxylic acid;
  4,4-oxybis(benzoic) acid;
  5-ter-butyl-1,3-benzenedicarboxylic acid, etc. . . .

In other words, the invention can also be defined as consisting of a process for producing aromatic dicarboxylates of an alkali metal of the type indicated above, in particular sodium, from the corresponding recovered aromatic dicarboxylic acid polyesters, and alkylene glycols, comprising a step for saponification of said polyesters using an aqueous alkali metal hydroxide solution, characterized by:

using an alkali metal hydroxide in said saponification reaction with an initial hydroxide weight content of the order of 20% to of the order of 45% by weight;

carrying out the reaction at a temperature in the range from about 120° C. to the boiling point of the corresponding alkylene glycol, if necessary at a pressure enabling the liquid phase of the reaction medium to remain in the liquid phase or at the boiling point at said temperature, throughout the saponification period;

then by adding to the mixture a volume of water sufficient to ensure dissolution of all of the alkali metal aromatic dicarboxylate produced in the liquid phase of the reaction medium.

The preferred conditions discussed above regarding poly (alkylene terephthalates) can also be envisaged for the treatment of alkylene polyesters of aromatic dicarboxylic acids.

What is claimed is:

1. A process for producing an alkali metal aromatic dicarboxylate and an alkylene glycol from a polyester of an aromatic dicarboxylic acid derived from a dicarboxylic acid forming a soluble salt with alkali metal comprising the steps of:

carrying out an alkaline saponfication by reacting said polyester with an alkali metal hydroxide in a liquid medium at a reaction temperature in the range of about 120° C. to the boiling point of the corresponding alkylene glycol;

adding a volume of water which is sufficient to ensure dissolution of all of the alkali metal aromatic dicarboxylate produced in the liquid phase of the reaction medium;

concentrating the solution by evaporating off water to cause a major portion of the alkali metal dicarboxylate to crystallize out of the liquid phase then charged with alkylene glycol, wherein the step of concentrating the solution by evaporating off water comprises crystallizing the alkali metal dicarboxylate out of the solution at a temperature of 50° C. to 90° C. under partial vacuum; and recovering said alkali metal aromatic dicarboxylate and said alkylene glycol.

2. A process according to claim 1, wherein said alkali metal aromatic dicarboxylate is an alkali metal terephthalate, and wherein said polyester is recovered poly (alkylene terephthalate), comprising the steps of:

saponification of said alkylene terephthalates using an aqueous solution of an alkali metal hydroxide, with an initial hydroxide concentration of the order of 20% to of the order of 45% by weight;

carrying out the reaction at a temperature in the range about 120° C. to the boiling point of the alkylene glycol produced, at a pressure which maintains the liquid phase of the reaction medium in a liquid state or at the boiling point at said temperature, throughout the step of saponification;

adding a volume of water sufficient to ensure dissolution of all of the alkali metal terephthalate produced in the liquid phase of the reaction medium.

3. A process according to claim 1, comprising crystallizing from said solution after pre-concentration of said solution at a temperature of the order of 100° C.

4. A process according to claim 1, further comprising the step of gradually introducing a recovered alkylene dicarboxylate in a divided state into an aqueous solution of alkali metal hydroxide at boiling point, at said reaction temperature.

5. A process according to claim 1, wherein the alkali metal hydroxide is sodium hydroxide.

6. A process according to claim 1, wherein the temperature is in the range of 125° C. to 160° C. and the alkali metal hydroxide is sodium hydroxide in a concentration range of 35% to 45% by weight.

7. A process according to claim 1, wherein the proportion of alkali metal hydroxide with respect to the alkylene dicarboxylate is in the range 0.8 times the stoichiometry to 1.5 times the stoichiometry.

8. A process according to claim 7, wherein the proportion of alkali metal hydroxide with respect to alkylene dicarboxylate is in the range from 0.8 stoichiometry to 1.2 times the stoichiometry.

9. A process according to claim 1, wherein said recovery of said alkali metal aromatic dicarboxylate comprises the step of acidifying mother liquors obtained after crystallizing the alkali metal dicarboxylate, which still contain dissolved sodium terephthalate and precipitating terephthalic acid.

10. A process according to claim 9, further comprising the step of recycling at least a portion of the precipitated terephthalic acid to the step for dissolving the alkali metal terephthalate formed, following said saponification.

11. A process according to claim 9, further comprising the steps of neutralizing acid sodium sulphate obtained after precipitating the terephthalic acid using an alkali hydroxide solution by concentrating the solution at a temperature enabling evaporation of a major portion of the water, maintaining the alkylene glycols in solution; separating a salt; and recovering a technical grade polyalkylene glycol.

12. A process according to claim 1, further comprising the step of recycling condensates produced in the concentration step to the step for dissolving the sodium terephthalate produced in the reaction medium.

13. A process according to claim 1, wherein said alkali metal is sodium.

14. A process according to claim 1, comprising carrying out the alkaline saponification at a pressure which maintains the liquid phase of the reaction medium in the liquid state or at the boiling point at said temperature.

15. A process according to claim 1 comprising adding a volume of water which is sufficient to ensure dissolution at the end of the reaction of all of the alkali metal aromatic dicarboxylate produced in the liquid phase of the reaction medium.

16. A process according to claim 15 comprising adding a volume of water which is sufficient to ensure dissolution at the end of the reaction of all of the alkali metal aromatic dicarboxylate produced in the liquid phase of the reaction medium after separating insoluble matter.

17. A process according to claim 4, wherein said recovered alkylene dicarboxylate is in a ground state.

18. A process according to claim 9, comprising acidifying said mother liquors with sulphuric acid.

19. A process according to claim 11, wherein said alkali hydroxide solution is sodium hydroxide.

20. A process according to claim 11, wherein the salt which is separated is sodium sulphate.

* * * * *